(12) United States Patent
Kronestedt

(10) Patent No.: US 8,038,649 B2
(45) Date of Patent: Oct. 18, 2011

(54) AUTOMATIC INJECTION DEVICE WITH NEEDLE INSERTION

(75) Inventor: Victor Kronestedt, Stockholm (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 12/678,145

(22) PCT Filed: Sep. 8, 2008

(86) PCT No.: PCT/EP2008/061863
§ 371 (c)(1),
(2), (4) Date: Nov. 19, 2010

(87) PCT Pub. No.: WO2009/037141
PCT Pub. Date: Mar. 26, 2009

(65) Prior Publication Data
US 2011/0106008 A1     May 5, 2011

Related U.S. Application Data

(60) Provisional application No. 60/973,193, filed on Sep. 18, 2007.

(30) Foreign Application Priority Data

Sep. 18, 2007  (SE) ...................... 0702084

(51) Int. Cl.
*A61M 5/20*           (2006.01)
(52) U.S. Cl. ....................................... 604/131
(58) Field of Classification Search .................. 604/110, 604/130, 131, 134, 135, 136, 137
See application file for complete search history.

(56) References Cited

U.S. PATENT DOCUMENTS

| 5,104,380 | A * | 4/1992 | Holman et al. | 604/117 |
| 5,611,491 | A * | 3/1997 | Bowers | 239/582.1 |
| 7,112,187 | B2 * | 9/2006 | Karlsson | 604/187 |
| 7,357,790 | B2 * | 4/2008 | Hommann et al. | 604/198 |
| 7,563,252 | B2 * | 7/2009 | Marshall et al. | 604/187 |
| 7,635,351 | B2 * | 12/2009 | Peter | 604/151 |
| 7,967,772 | B2 * | 6/2011 | Mckenzie et al. | 604/19 |
| 2005/0203466 | A1 * | 9/2005 | Hommann et al. | 604/240 |
| 2006/0167413 | A1 * | 7/2006 | Marshall et al. | 604/110 |

(Continued)

FOREIGN PATENT DOCUMENTS

DE      10359694 A1 *   7/2005

(Continued)

*Primary Examiner* — Nicholas D Lucchesi
*Assistant Examiner* — Aarti B Berdichevsky
(74) *Attorney, Agent, or Firm* — Potomac Patent Group PLLC

(57) ABSTRACT

The present invention relates to an injection device comprising a housing (10, 100), a container holder (12) arranged within said housing having a container (20) adapted to contain medicament to be delivered through a needle, plunger drive means (40), an energy accumulating member (80) adapted to accumulate and transfer energy to said plunger drive means wherein said device further comprises container driver means (30) arranged and designed to be connected to the plunger drive means and to the container holder for holding the container and its needle stationary within said housing before said energy is provided to the drive means and for urging the container towards the proximal end of the device when said energy is provided to the drive means whereby a needle penetration and respectively an injection are performed.

16 Claims, 6 Drawing Sheets

U.S. PATENT DOCUMENTS

| | | | |
|---|---|---|---|
| 2006/0287630 A1* | 12/2006 | Hommann | 604/130 |
| 2007/0167920 A1* | 7/2007 | Hommann | 604/206 |
| 2010/0222742 A1* | 9/2010 | Hogdahl | 604/135 |
| 2010/0249705 A1* | 9/2010 | Kronestedt | 604/134 |

FOREIGN PATENT DOCUMENTS

| | | | |
|---|---|---|---|
| EP | 728529 A2 * | 8/1996 | |
| WO | WO 2004028598 A1 * | 4/2004 | |
| WO | WO 2005002653 A1 * | 1/2005 | |

* cited by examiner

AUTOMATIC INJECTION DEVICE WITH NEEDLE INSERTION

TECHNICAL FIELD

The present invention relates to an injection device having several automatic functions such as automatic penetration, automatic injection and automatic safety means for preventing from accidental needle sticks and in particular an injection device capable of handling medicament in fluid form having high viscosity.

BACKGROUND ART

The present invention relates to injection devices for injecting medicament in fluid form having high viscosity which means that these devices require high forces in order to press the fluid through a needle when injecting the medicament.

Auto-injectors, or pen-injectors have been on the market for many years. One of the first auto-injectors was developed for war-times, which was activated by pressing the injector against a body part for activating it. The main concern was to have the medicament injected as fast as possible, without much concern for the patient or for handling safety aspects. During the recent years some medicaments have been developed such that these have to be injected by the patients themselves. Therefore, depending on the intended use and type of medicament, it has also been developed injection devices having a varying degree of automatic functions to facilitate the injection of medicaments in a reliable and safe way for patients and even for trained personnel; e.g. physicians, nurses.

Auto-injector devices having an automated injection function often comprises a housing, a spirally wound compression spring acting on a plunger rod which in its turn acts on a stopper inside a medicament container for expelling the medicament through an attached needle to the container. Normally, one end of the spring is often abutting an inner end surface of the housing, which means that the housing has to be dimensioned to the force of the spring. When fluids with high viscosity are to be injected using an auto-injector, high forces are required to expel the medicament through a fine needle. Consequently, the spring becomes very large both regarding the diameter of the wound spring and also the diameter of the thread of the wire. The size of the spring means that the device becomes large, and for some applications and customers, such sizes of the devices are not acceptable.

A solution to said problem is disclosed in document EP 1 728 529 which discloses a medicament delivery device arranged with an energy accumulating member, e.g. a flat spiral spring, capable of providing an output torque to a plunger rod driving member which is adapted to engage a threaded plunger rod. The rotation of the plunger rod driving member due to the output torque of the spring rotates the plunger rod and allows said rod to be driven forwardly within a medicament container for expelling said medicament. When said device is used as an injection device; a user e.g. a patient, a physician or trained personal; has to penetrate the needle manually. Though, said device comprises a needle shield sleeve for activating the injection step and for covering the needle after the medicament has been injected, some users experience this manually penetration as an unpleasant step.

A solution to this problem is disclosed in document U.S. Pat. No. 5,104,380 which discloses an injection device having a rotatable dose metering cap which compresses a coil spring. When a dose is to be injected, a latch body is pressed against an injection site such that a compression spring can be decompressed for performing an auto-penetration. That action also brings a drive gear out of engagement permitting the coil spring to unwind and thereby rotating a drive plunger rod. Said rotational movement is accompanied by axial movement to cause medicament to be discharged from a cartridge and injected through a needle. This design cannot be utilised when larger forces for injecting a high viscous medicament are required. This design also requires an extra latch body comprising an extra spring for auto-penetration, which increases the physical size and manufacturing cost for such device.

DISCLOSURE OF THE INVENTION

The aim of the present invention is to provide injection device having several automatic functions as automatic penetration, automatic injection and automatic safety means for preventing accidental needle sticks and in particular an injection device capable of handling medicament in fluid form having high viscosity without increasing the size of the injector in any substantive way.

This aim is obtained with an injector according to the features of claim 1. Preferable embodiments of the invention are the subject of the dependent claims.

According to a main aspect of the invention it is characterised by an injection device comprising a housing, a container holder arranged within said housing having a container adapted to contain medicament to be delivered through a needle attached to the container and a stopper sealingly and slidable arranged inside said container, an energy accumulating member arranged in the interior of the device and adapted to accumulate energy, plunger drive means comprising a plunger rod driving member connected to said energy accumulating member and threadly engaged to a plunger rod which is arranged with a proximal end in contact with said stopper, such that when said plunger rod driving member is rotated due to an output torque from the energy accumulating member, the plunger rod (40) is urged towards the proximal end of the device, characterized in that said device further comprises container driver means arranged and designed to be fixedly connected to the container holder and to be releasably connected to the plunger rod, such that when said plunger rod is urged towards the proximal end of the device, the container holder is moved a predetermined distance towards the proximal end of the device whereby a needle penetration is performed and whereupon the continuous movement of said plunger rod forces said container driver means to be released from said plunger rod whereby an injection is performed.

According to another aspect of the invention, said container driver means is connected to the plunger drive means in a snap-on fit manner for releasing said container driver means from said driver means and thereby said container holder from the force that urges it towards the proximal end of the device, directly after the needle penetration is performed.

According to yet another aspect of the invention, said container driver means comprises resilient members arranged in snap-on fit manner in an annular groove on said plunger rod for releasing said container driver from said plunger rod directly after the needle penetration is performed and for allowing said container driver to slide over said plunger rod when said plunger rod continues to be driven towards the proximal end of the device inside said container for expelling the medicament through said needle.

According to another aspect of the invention, said plunger drive means further comprises non-rotating means arranged and designed to be engaged to longitudinal guiding means on the plunger rod for urging the plunger rod to move linearly inside said container towards the proximal end of the device.

According to a further aspect of the invention, said device further comprises holding means capable of acting on said plunger drive means for holding said energy accumulating member in a loaded state.

According to yet another aspect of the invention, it further comprises actuating means capable of acting on said holding means for releasing said energy accumulating member and thereby said plunger drive means.

According to a further aspect of the invention, it further comprises a needle shield sleeve arranged slidable in said proximal housing capable of acting on said actuating means when said needle shield sleeve is pressed against an injection site.

According to yet an aspect of the invention, said actuating means further comprises a resilient means for urging said needle shield sleeve towards the proximal end of the device when said device is removed from the injection site.

According to yet an aspect of the invention, said device further comprises a locking means for locking said needle shield sleeve against moving towards the distal end of the device when said device is removed from the injection site.

The advantages with the present invention are several. Because the device is arranged with an energy accumulating member which provides a torque force, a large force can be obtained. The device is thus capable of handling liquid medicament having high viscosity, without the device having to be large and bulky, and thus not very attractive to users.

Also, the device requires only one energy accumulating member for performing both an automatic penetration and an injection function.

These and other aspects of and advantages with the present invention will become apparent from the following detailed description and from the accompanying drawings.

BRIEF DESCRIPTION OF DRAWINGS

In the following detailed description of the invention, reference will be made to the accompanying drawings, of which

DETAILED DESCRIPTION OF THE INVENTION

In the present application, when the term "distal part/end" is used, this refers to the part/end of the injection device, or the parts/ends of the members thereof, which under use of the injection device is located the furthest away from the medicament injection site of the patient. Correspondingly, when the term "proximal part/end" is used, this refers to the part/end of the injection device, or the parts/ends of the members thereof, which under use of the injection device is located closest to the medicament injection site of the patient.

Figure 6:
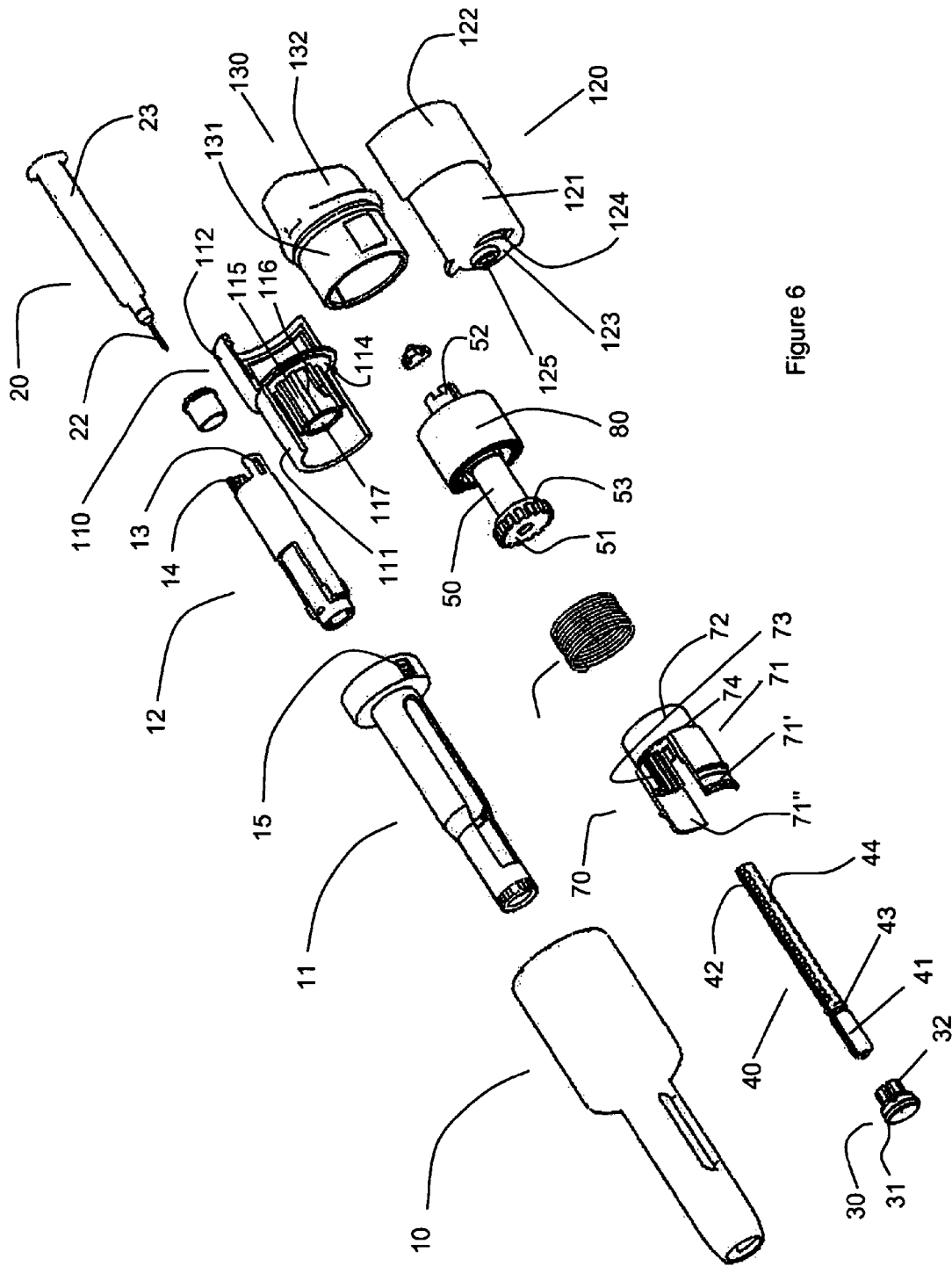
FIG. 6 is an exploded view of the injector of FIG. 1.

The embodiment of the injector shown in the drawings comprises a housing having a proximal housing 10 and a distal housing 100, an elongated needle shield sleeve 11, a container driver 30, a plunger rod 40, a plunger rod driving member 50, a helical spring 60, an actuating sleeve 70 and an energy accumulating member 80. The proximal housing 10 being an elongated tube-shaped comprising of two sections: a proximal section and a distal section, wherein the distal section has a diameter that is larger than the diameter of the proximal section. The elongated needle shield sleeve 11 comprises of three sections: a proximal section a middle section and a distal section, wherein the distal section has a diameter that is larger than the diameter of the middle section and the middle section has a diameter that is larger than the diameter of the proximal section, as seen in FIG. 6. Said elongated needle shield sleeve 11 is slidably arranged within said elongated housing, wherein a portion of the proximal end of said needle shield sleeve protrudes out of the proximal housing 10, which is pressed against the injection site during use, as will be described below. Further said needle shield sleeve comprises in the circumference of its distal section resilient tongues 15.

Inside the needle shield sleeve a medicament container holder 12 is arranged and inside the container holder a container 20, e.g. a cartridge, a syringe or the like, is arranged containing medicament to be delivered through a needle 22 attached to the container and a stopper 23 sealingly and slidable arranged inside said container. Moreover, the distal part of the container holder is arranged with tongues 13 having inwardly directed ledges 14, as seen in FIG. 6.

Between the tongues 13 of said medicament container holder 12, a funnel-shaped annular member 30, hereinafter called container driver, is arranged. Said container driver comprises in its proximal end and in its outer surface one outwardly directed annular ledge 31 which cooperates with the ledges 14 of the container holder creating a snap-on fit between these components. From the proximal end of said container driver extends at least two resilient members 32, e.g. tongues, legs; towards the distal end, wherein each member 32 comprises an inwardly directed ledge 33.

The plunger rod 40 is provided in the interior of the injection device, running along the longitudinal axis of said device. Said plunger rod comprises two of sections: a distal section 42 and a proximal section 41, wherein the distal section has a diameter that is smaller than the diameter of the proximal section, wherein the distal section has a length that is larger than the length of the proximal section and wherein the distal section is threaded and comprises longitudinal guiding means 44. Moreover, an annular groove 43 is arranged at the distal end of the proximal section 41 of said plunger rod 40 wherein said annular groove 43 cooperates with the ledges 33 of said container driver 30 creating a snap-on fit between these components. Further, the proximal end of the proximal section 41 is in contact with the stopper 23 in the medicament container.

The threaded distal section 42 of the plunger rod 40 is screw threaded in the interior of the plunger rod driving member 50. Said driving member 50 comprises of two sections: a distal section 52 and a proximal section 51, wherein the distal section 52 has a diameter that is smaller than the diameter of the proximal section 51 and a length than is larger than then length of the proximal section 51. Further, the proximal section 51 comprises outwardly protruding flanges or teeth 53, as seen in FIG. 6.

In a preferred embodiment, the distal housing 100 comprises of three housings: a first half distal housing 110, a second half distal housing 120 and a third distal housing 130 adapted to house the plunger rod driving member 50, a helical spring 60, the actuating sleeve 70 and the energy accumulating member in the form of e.g. a flat spiral spring 80, a helical torque spring.

Said first half distal housing 110 comprises of two sections: a distal section 112 and a proximal section 111, wherein the distal section has a diameter that is larger than the diameter of the proximal section. The distal section 112 is divided from the proximal section 111 by a member, which comprises a disc-like part 114 in its distal end and a coaxially part 115 in its proximal end forming a cylindrical space, in which said helical spring 60 is arranged having its distal end supported against the disc-like part 114. Said coaxially part 115 comprises outwardly protruding flanges 116 on its outer surface and a through going hole 117 adapted to house a portion of the distal 52 section of the plunger rod driving member 50. At least two of said outwardly protruding flanges 116 have resilient arms 118.

Said second half distal housing 120 comprises of two sections: a distal section 122 and a proximal section 121, wherein the distal section 122 has a diameter that is larger than the diameter of the proximal section 121. Further, said second half distal housing 120 also comprises a proximal end wall 123 having a two crescent apertures 124 and a through going hole 125 provided with non-rotating interior means (not shown) adapted to travel along the longitudinal guiding means 44 of the plunger rod 40.

The third distal housing 130 also comprises a distal section 132 and a proximal section 131, wherein the distal section 132 has an inner diameter that is smaller than the inner diameter of the proximal section 131. The distal section 132 is thus adapted to house a portion of the distal 52 section of the plunger rod driving member 50 and the proximal section 131 is adapted to house the flat spiral spring 80. Said flat spiral spring 26 is provided with outer holding means in order to be connected to the proximal section 131 of the third distal housing 130 and with inner holding means in order to be attached to the distal section 52 of the plunger rod driving member 50. Moreover, in a preferred embodiment, the proximal section 131 of the third distal housing 130 is arranged to be manually rotatable between the distal sections 112 and 122.

The actuating sleeve 70 comprises of two sections: a distal section 72 and a proximal section 71, wherein the distal section 72 is a ring and the proximal section are two tongues 71', 71". Both sections 71, 72 arranged between the first half distal housing 110 and the second half distal housing 120. The distal section 72 has an outer diameter that is smaller than the outer diameter of the proximal section 71 forming two support walls 74 where the proximal end of the helical spring 60 is supported. Said tongues 71', 71" extends towards the proximal end of the device through the crescent apertures 124 of the second half distal housing 120 and comprises on its outer surface some ledges that mates with resilient tongues 15 of the needle shield sleeve 11. Further, said sections 71 and 72 comprises inwardly directed ledges forming slots 73, as seen in FIG. 6, which mate the outwardly protruding flanges 53 of the plunger rod driving member 50 and the outwardly protruding flanges 116 of the first half distal housing 110.

Figure 1:
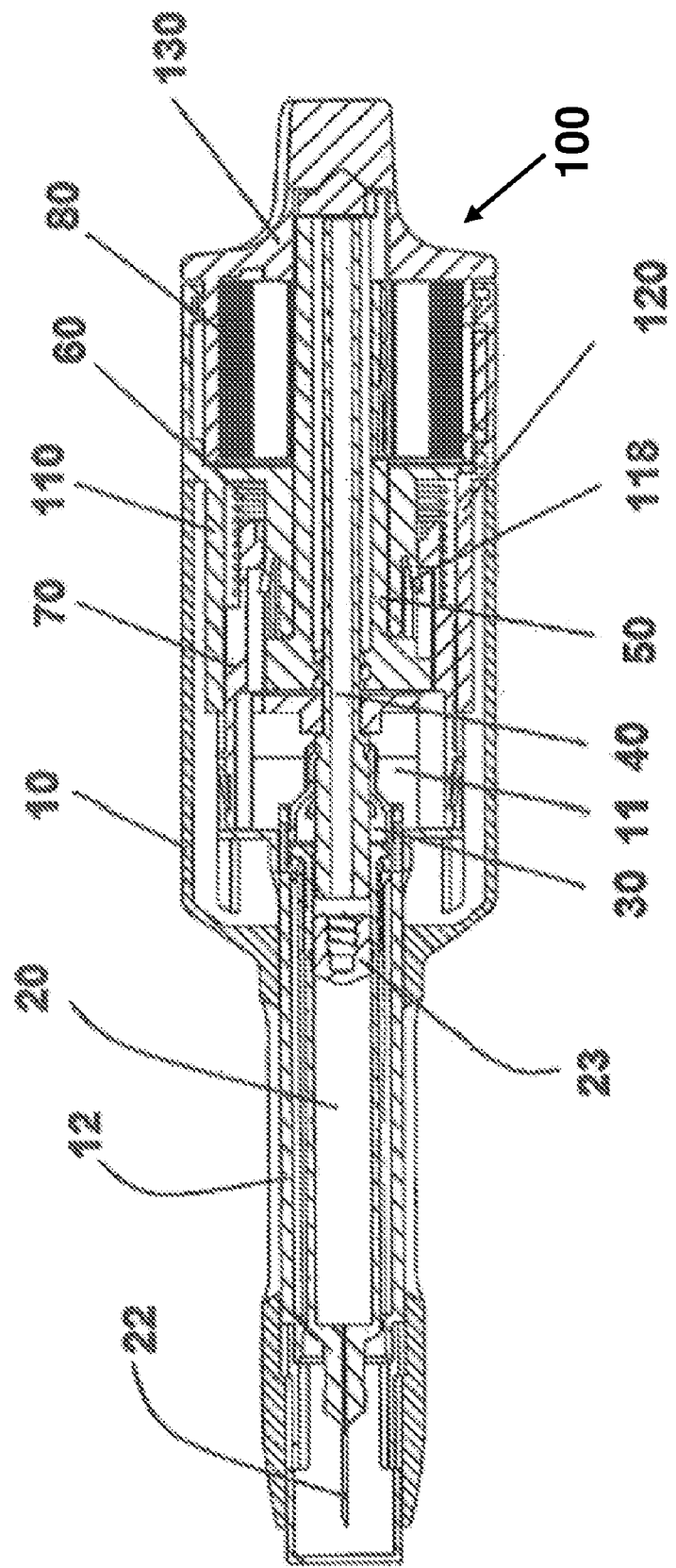
FIG. 1 is a cross-sectional view of an injector according to the present invention in a state when delivered to a user.

The device is intended to function as follows. When the device is delivered to a user, in a preferred embodiment, the flat spiral spring 80 has been already loaded at the manufacturing site. In another embodiment the flat spiral spring 80 is loaded by the user through rotating the third distal housing 130. Further, a protective cap (not shown) is arranged at the proximal end of the device. The protective cap comprises a sheath (not shown) covering the needle in a sterile way. When the cap is removed, so is also the sheath. This also causes the needle shield sleeve 11 to move towards the proximal end of the device and protrude somewhat at the proximal end of the injector, FIG. 1.

Figure 2:
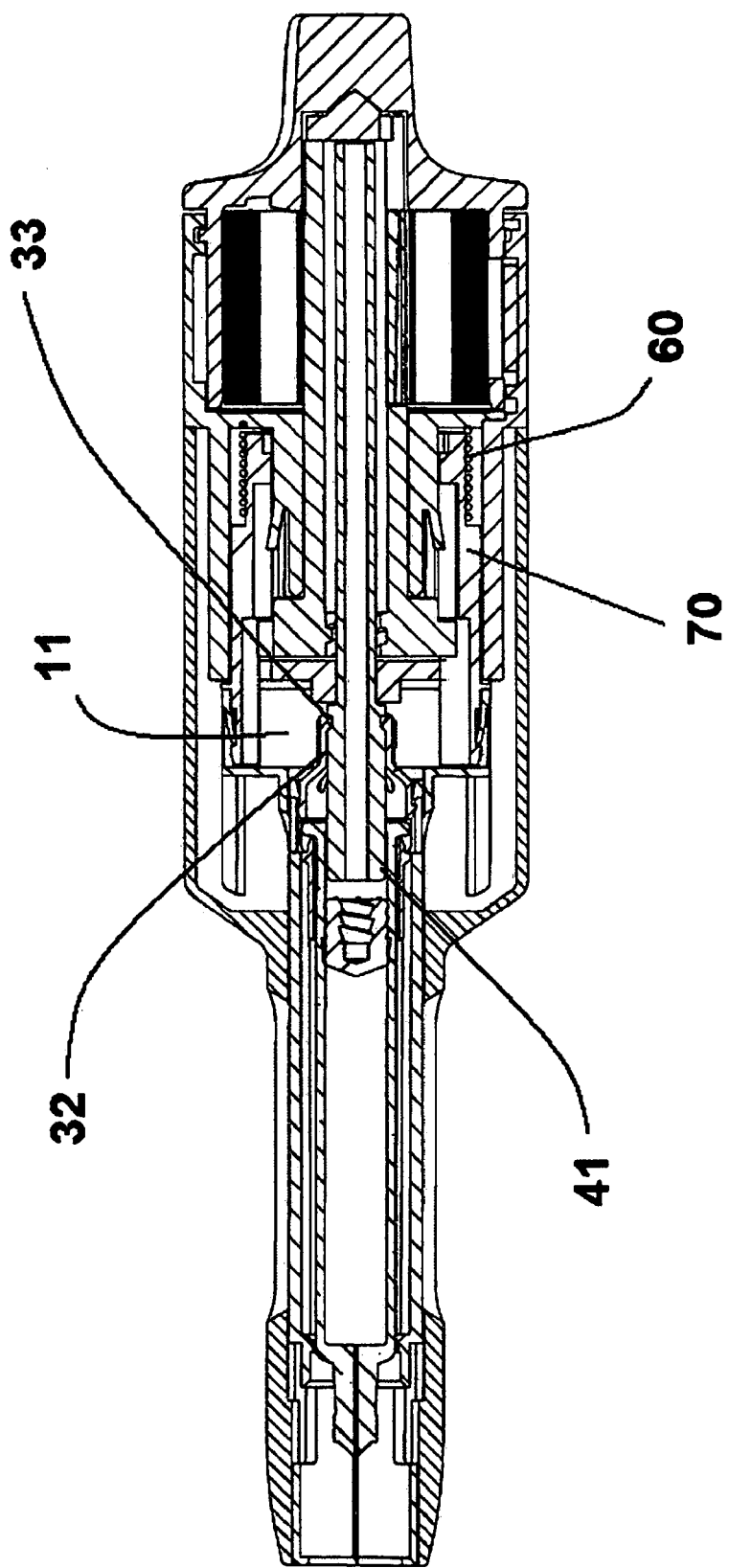
FIG. 2 is a cross-sectional view of the injector of FIG. 1 where penetration has been initiated.
Figure 3:
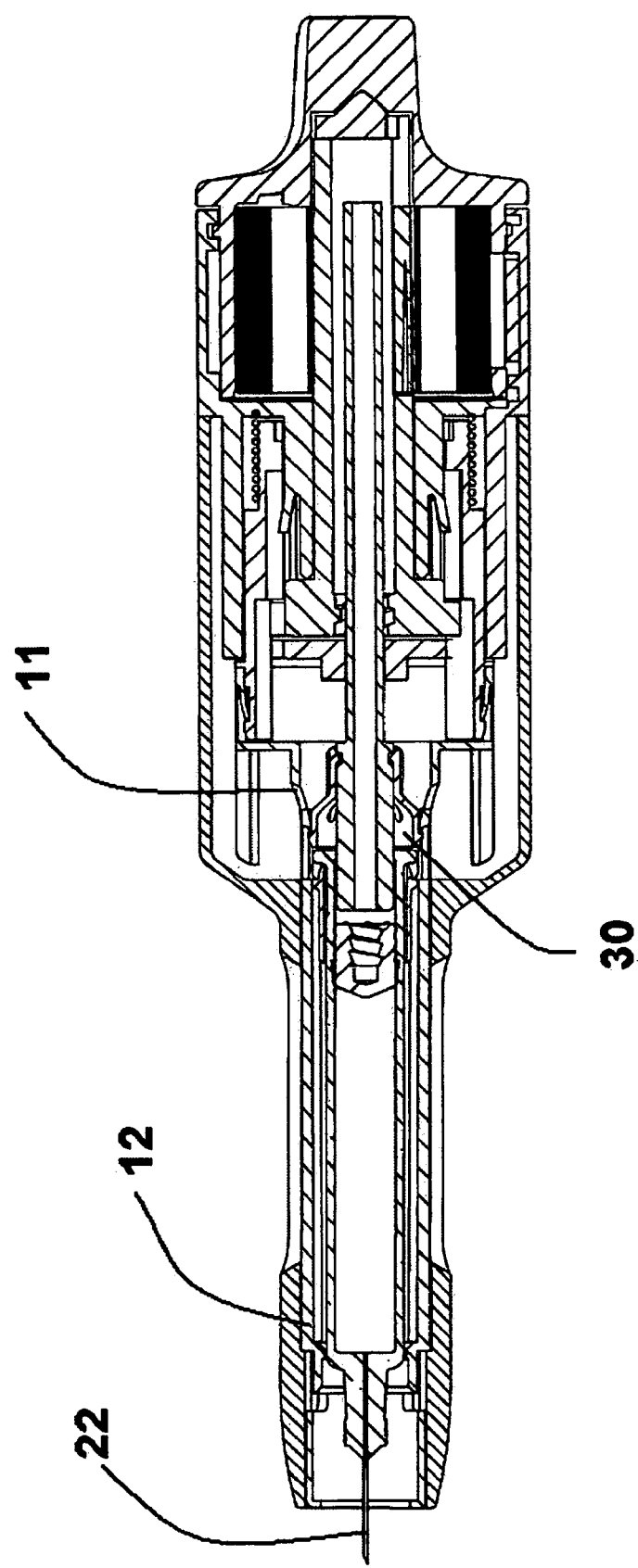
FIG. 3 is a cross-sectional view of the injector of FIG. 1 where penetration has been completed.

The injector is now ready to use. The proximal end of the needle shield sleeve 11 is pressed against the injection site, whereby the needle shield sleeve is pushed towards the distal end of the device, FIG. 2. Since the needle shield sleeve is connected to the actuating sleeve 70, the latter is also moved towards the distal end of the device, whereby the helical spring 60 is compressed and the inwardly directed ledges forming slots 73 of the actuation sleeve 70 and the outwardly protruding flanges 53 of the plunger rod driving member 50 are brought out of engagement whereby the plunger rod driving member 50 is released for rotation due to the energy accumulated in the flat spiral spring 80. The rotation of the plunger rod driving member 50 will rotate the plunger rod 40, and due to the non-rotating interior means provided in the through going hole 125 adapted to travel along the longitudinal guiding means 44 of the plunger rod 40, the plunger rod is linearly urged towards the proximal end of the device without rotation.

When the plunger rod is linearly urged towards the proximal end of the device, the medicament container holder 12 is also urged towards the proximal end of the device, due to the engagements 14, 31, 32, 43 between the medicament container holder 12, the container driver 30 and the plunger rod 40. The movement of the medicament container holder 12 causes the automatic penetration of the needle 22 into the injection site.

Figure 4:
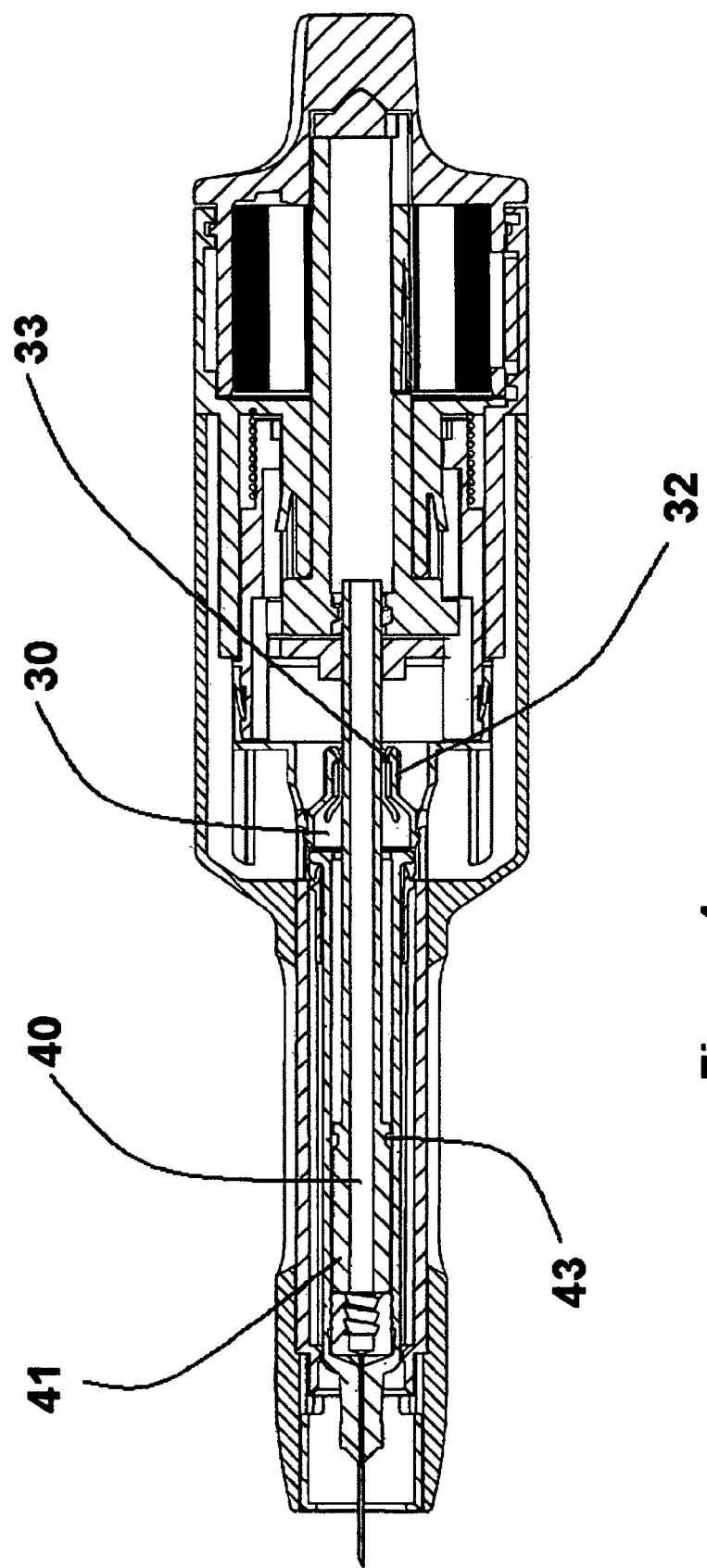
FIG. 4 is a cross-sectional view of the injector of FIG. 1 where injection has been completed.

The needle 22 is completely penetrated until the proximal end of the medicament container holder 12 comes into contact with the transition part between the proximal section and the middle section of the needle shield sleeve 11. The torque force of the spring 80 will continue to drive the plunger rod further towards the proximal end of the device inside the container pressing the stopper 23 in order to start expelling the medicament through the passage of the needle 22. Said movement takes out of contact the inwardly directed ledges 33 of the container driver 30 which cooperates with the annular groove 43 of the plunger rod 40 for releasing the container driver from the plunger rod and thereby the container/container holder from the force that urges it towards the proximal end of the device. The container driver slides over along the plunger rod as said plunger rod continues to move towards the proximal end of the device. The injection is completed when the stopper is at the proximal end of the container, FIG. 4.

Figure 5:
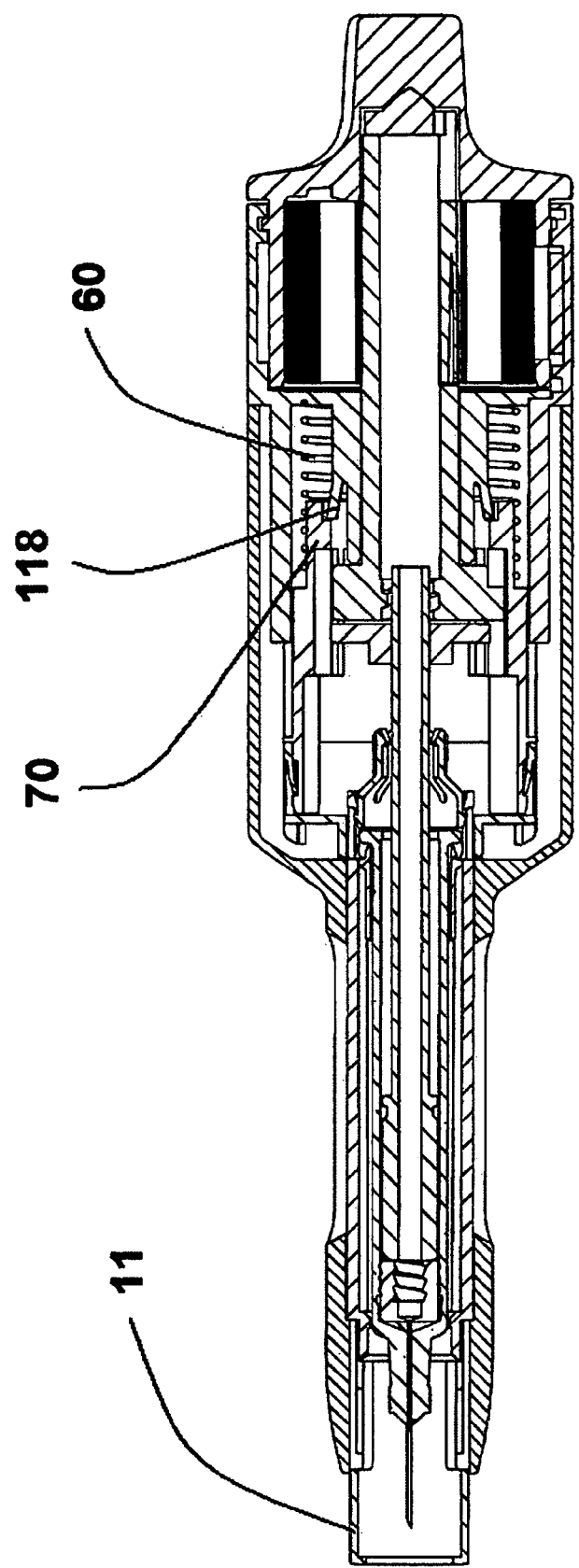
FIG. 5 is a cross-sectional view of the injector of FIG. 1 where the injector has been withdrawn from the injection site.

The device may now be removed from the injection site. The spring 60 acting on the actuation sleeve 70 will cause the needle shield sleeve 11 to move forward, FIG. 5, since the needle shield sleeve is connected to the actuating sleeve, thereby covering the needle. The resilient arms 118 are thus free to flex out radially whereby they come into contact with the distal wall of the actuation sleeve 70 and thereby locking said needle shield sleeve 11 such that said needle shield sleeve 11 cannot be pushed again towards the distal end of the device.

The device is now ready to be discarded.

It is to be understood that the embodiment described above and shown in the drawings is to be regarded only as non-limiting examples of the present invention and that it may be modified within the scope of the patent claims.

The invention claimed is:

1. An injection device, comprising:
 a housing;
 a container holder arranged within said housing having a container adapted to contain medicament to be delivered through a needle attached to the container and a stopper sealingly and slidably arranged inside said container;
 an energy accumulating member arranged in the interior of the device and adapted to accumulate energy;
 a plunger drive mechanism, comprising a plunger rod driving member connected to said energy accumulating member and threadedly engaged to a plunger rod having a proximal end in contact with said stopper, and a non-rotating device arranged to be engaged to a longitudinal guide device on the plunger rod such that when said plunger rod driving member is rotated due to an output torque from the energy accumulating member, the plunger rod is linearly urged toward a proximal end of the device; and
 a container driver mechanism arranged to be fixedly connected to the container holder and to be releasably connected to the plunger rod, such that when said plunger rod is urged towards the proximal end of the device, the container holder is moved a predetermined distance toward the proximal end of the device, whereby a needle penetration is performed and whereupon continuous movement of said plunger rod forces said container driver mechanism to be released from said plunger rod whereby an injection is performed.

2. The injection device of claim 1, wherein said container driver mechanism comprises resilient members arranged by a snap-on fit in an annular groove on said plunger rod for releasing said container driver from said plunger rod directly after the needle penetration is performed and for allowing said container driver mechanism to slide over said plunger rod when said plunger rod continues to be driven toward the proximal end of the device inside said container for expelling the medicament through said needle.

3. The injection device of claim 1, further comprising a holder configured to act on said plunger drive mechanism for holding said energy accumulating member in a loaded state.

4. The injection device of claim 3, further comprising an actuator configured to act on said holder for releasing said energy accumulating member and thereby said plunger drive mechanism.

5. The injection device of claim 4, further comprising a needle shield sleeve slidably arrange in said proximal housing and configured to act on said actuator when said needle shield sleeve is pressed against an injection site.

6. The injection device of claim 5, wherein said actuator comprises a resilient device configured to urge said needle shield sleeve towards the proximal end of the device when said device is removed from the injection site.

7. The injection device of claim 6, further comprising a locking device configured to lock said needle shield sleeve against movement toward a distal end of the device when said device is removed from the injection site.

8. The injection device of claim 1, wherein the energy accumulating member is a flat spiral spring.

9. The injection device of claim 1, wherein said container driver mechanism is connected to the plunger drive mechanism by a snap-on fit for releasing said container driver mechanism from said plunger rod and thereby said container holder from the force that urges it toward the proximal end of the device, directly after the needle penetration is performed.

10. The injection device of claim 9, wherein said container driver mechanism comprises resilient members arranged by a snap-on fit in an annular groove on said plunger rod for releasing said container driver from said plunger rod directly after the needle penetration is performed and for allowing said container driver mechanism to slide over said plunger rod when said plunger rod continues to be driven toward the proximal end of the device inside said container for expelling the medicament through said needle.

11. The injection device of claim 9, wherein the energy accumulating member is a flat spiral spring.

12. The injection device of claim 9, further comprising a holder configured to act on said plunger drive mechanism for holding said energy accumulating member in a loaded state.

13. The injection device of claim 12, further comprising an actuator configured to act on said holder for releasing said energy accumulating member and thereby said plunger drive mechanism.

14. The injection device of claim 13, further comprising a needle shield sleeve slidably arrange in said proximal housing and configured to act on said actuator when said needle shield sleeve is pressed against an injection site.

15. The injection device of claim 14, wherein said actuator comprises a resilient device configured to urge said needle shield sleeve towards the proximal end of the device when said device is removed from the injection site.

16. The injection device of claim 15, further comprising a locking device configured to lock said needle shield sleeve against movement toward a distal end of the device when said device is removed from the injection site.

* * * * *